United States Patent [19]

McAdams

[11] Patent Number: 5,690,658
[45] Date of Patent: Nov. 25, 1997

[54] KERATOREFRACTIVE SYSTEM AND METHOD

[76] Inventor: John B. McAdams, 22107 Boca Place Dr., Boca Daton, Fla. 33433

[21] Appl. No.: 453,906

[22] Filed: May 30, 1995

Related U.S. Application Data

[63] Continuation of Ser. No. 132,374, Oct. 6, 1993, abandoned.
[51] Int. Cl.$^6$ ............................................. A61F 9/00
[52] U.S. Cl. ............................................. 606/166; 606/172
[58] Field of Search ............................. 606/166, 170, 606/172, 102; 128/774; 30/293, 294

[56] References Cited

U.S. PATENT DOCUMENTS

| | | | |
|---|---|---|---|
| 4,569,133 | 2/1986 | Schmidt | 30/293 |
| 5,411,511 | 5/1995 | Hall | 606/166 |

OTHER PUBLICATIONS

1980 American Hospital Supple Corp. American v. Mueller division p. 10 Su–Surgery: General.

*Primary Examiner*—Michael Buiz
*Assistant Examiner*—Kevin Truong
*Attorney, Agent, or Firm*—Francis G. Rushford

[57] ABSTRACT

A set of surgical instruments and a method for performing Keratorefractive eye surgery is disclosed. The set of surgical instruments includes two or more knife blades for making incisions of a precise depth in the cornea, and two or more footplate assemblies for holding each of the knife blades, the cutting portion of each knife blade extends from the footplate assembly by a precise fixed length corresponding to the precise depth of incision which can be made by that particular knife blade. Each footplate assembly includes a footplate which moves on the surface of the cornea to precisely control the depth of incision. Each footplate assembly also includes markers for indicating the range, fixed length and style of the knife blade, along with a handle for holding and manipulating each knife blade.

27 Claims, 3 Drawing Sheets

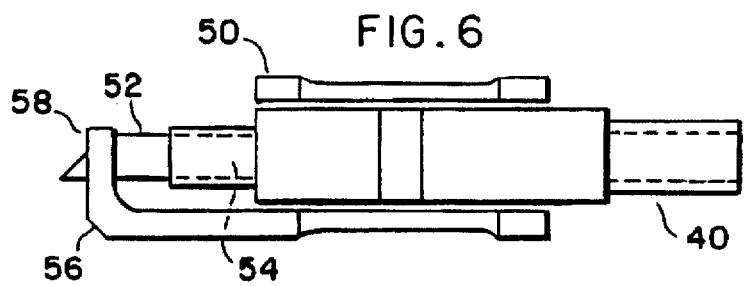
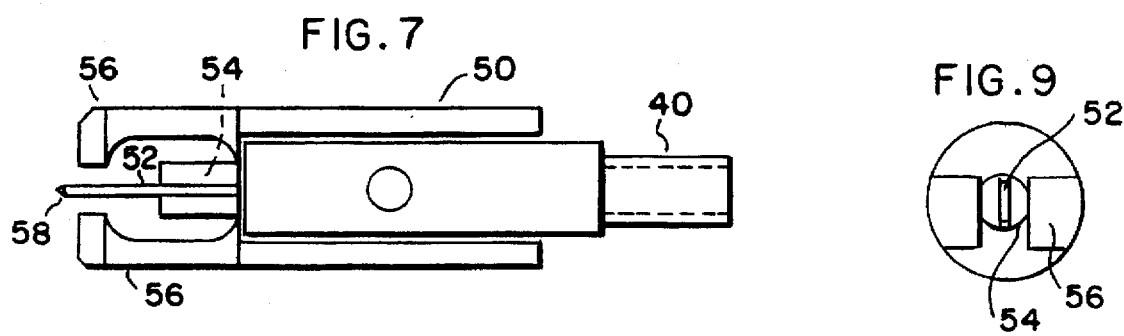
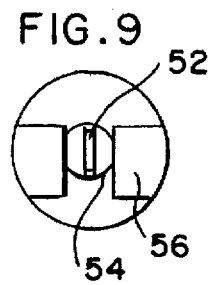
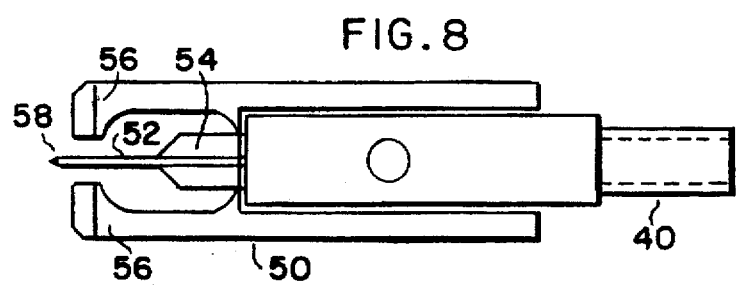
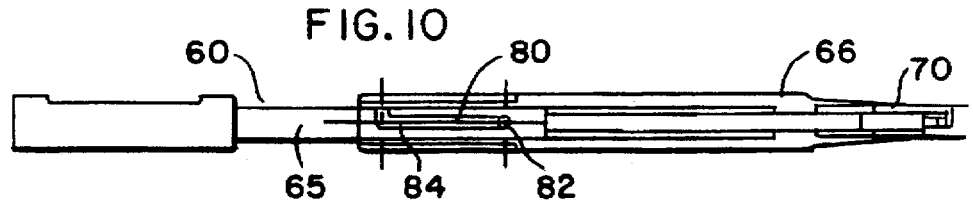
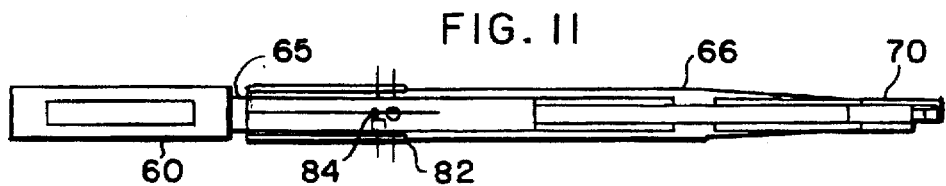
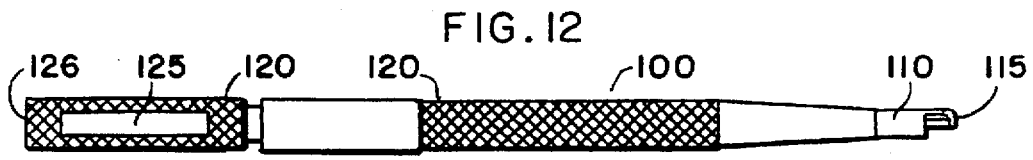

KERATOREFRACTIVE SYSTEM AND METHOD

This application is a continuation application of Ser. No. 08/132,374 filed on Oct. 6, 1993, now abandoned.

BACKGROUND OF THE INVENTION

The current invention relates to surgical blades for use in Keratorefractive eye surgery or all forms of incisional Keratotomy and a novel method for performing same. More particularly, the invention is directed towards a system or sets of surgical instruments have fixed length knife blades that allow for safer and more precise corneal incisions.

Keratorefractive surgery or incisional keratotomy involves changing the refraction of the eye's cornea by making incisions in, but not through the eye's cornea. In this type of surgery, the goal is to change the shape of the cornea by making plurality of incisions in the cornea. The procedure is known as either incisional Keratotomy or Keratorefractive surgery. The use of the term Keratorefractive surgery herein shall include all procedures involving corneal incisions made in order to affect or change the eye's vision or the cornea's refractive characteristics.

The goal of Keratorefractive surgery is to result in emmetropia. In emmetropia, no optical defects exists, lights rays entering the eye focus clearly on the retina. Defects in visions are common and correctable to the point of defect free vision through Keratorefractive surgery. In hyperopia or farsightedness, the most common refractive error, the point of focus of the rays of light entering the eye lies behind the retina because the eye's cornea curvature is too shallow. This refractive defect usually has been corrected by using a convex(plus) lens in glasses or contact lenses. In myopia or nearsightedness, which affects about twenty-five percent of the adult population in the United States, the image entering the eye is focused in front of the retina because the eye's cornea is curved too steeply. This defect usually has been corrected by using a concave(minus) lens in glass or contact lenses. In astigmatism, the refraction is unequal in different meridians or quadrants of the eye. The cornea in this optical defect is shaped more like the surface a football, rather than like surface of a basketball when astigmatism is not found. This defect usually has been corrected through the use of cylindric corrective lens (a segment cut from a cylinder), that has no refractive power along one axis and is concave or convex along the other axis.

In 1972, Dr. Syvatoslav Fyodorov introduced and began to practice a new eye surgery procedure that involved incisions in, but not through the eye's cornea. The Keratorefractive surgical procedure practiced by Dr. Fyodorov, primarily involved patients affected with myopia or nearsightedness. As a result of specific corneal incisions, Dr. Fyodorov was able to reduce or eliminate the myopia in many patients. By 1980, many successful keratorefractive surgical procedures were performed by Dr. Fyodorov. The surgical procedure developed by Dr. Fyodorov for treating myopia evolved with the corneal incisions being radial from the limbus to just before the optical zone. This procedure has become generally known as Radial Keratotomy (RK). Keratorefractive surgery has become very popular in the United States to correct vision problems. The RK, Astigmatic Keratotomy (AK) and the Hyperopia procedures are all growing in popularity as a way to correct defective vision. In some places and with some surgeons, the Hyperopia procedure has been designate as Hexagonal Keratotomy (HK) because in its initial practice the incisions in the cornea have been hexagonal. The Hyperopia procedure shall be referred herein through the use of HK, but it should not be read as being limited to hexagonal incisions because as Keratorefractive surgery develops the direction and the design or type of incisions will change. Therefore, HK shorthand herein will be for the general procedure or Hyperopic Keratotomy (HK).

A typical RK surgical procedure will illustrate the problems encountered with current system and procedure, and will help illustrate the benefits of the current invention. RK is selected by way of example, but the current invention is applicable to all Keratorefractive surgical procedures, including but not limited to AK and HK. The use of the current systems and problems, as well as the current invention is applicable to all procedures where correction of vision defects are being made through any and all type of cornea incisions. In RK, the myopic condition is minimized or eliminated as the result of a series of corneal incisions. The current practice is to make the incision radially along and in the cornea.

Exact incisions at a precise depth are critical to all the Keratorefractive surgical procedure. In Keratorefractive surgery the depth of penetration of the cutting blade must be controlled because the incision must not go through the cornea and perforate it. In Keratorefractive surgery, including RK, the cutting blade must cut to a depth of at least eighty-five percent of the total thickness of the cornea for the best result. The optimum incisions are those that are as deep as possible without causing the cornea to rupture, i.e., deep as possible without cutting all the way through the cornea. For practical reasons involving current practice, however, the depth of the incisions has been set at, at least eighty-five percent for a general rule of thumb.

During the RK procedure at patient's eye is anesthetized with a local anaesthetic. The eye is then held open with a lid speculum. A microscope is then placed over the patient's eye and the surgeon marks the patient's optical zone with a optical zone marker utilizing a marking dye. The incisions in Keratorefractive surgery are usually made only outside of the optical zone of the cornea. Then the surgeon measures the center of the patient's corneal thickness using a pachymeter. That reading could typically be 0.540 mm. The surgeon then marks the eye with a radial zone marker (that can any number of marking protrusions with the typical number has been four to eight) to mark the cornea with dye for the incisions. The knife has a micrometer screw control in its handle that will extend or retract the knife blade that will make the incisions. The typical knife has a blade together with a foot plate surroundablly attached to the knife around and adjacent to the knife blade. The footplate has a highly polished surface and rides along the surface of the cornea as the knife blade extends beyond the footplate cutting the cornea to a depth that will not result in perforations, sutures and the end of the operation.

The surgeon can take a number of measurements using a pachymeter in different areas of the cornea. The cornea's thickness changes from center to edge or limbus; the cornea getting thicker as the measurements are made from center to limbus. Also, the cornea changes thickness with quadrant, i.e. the quadrants being the areas defined by a simple x-y axis being superimposed over the cornea, The cornea thickness also changes due to the time of day, the humidity, and the quality of the air. Typically during the course of the day, the cornea will lose liquid or dehydrate and become thinner or increase its density. During the course of a Keratorefractive operation, the cornea can lose one percent of it thickness per minute. Therefore, the surgeon does not have a lot of time between measurements to make incisions.

The length of the knife blade from the footplate to the tip is typical set with the micrometer screw control. Because of the problems associated with screw controls, the blade's protruding length is often checked at least a second time by a nurse or technicians and often a third time by the surgeon. These calibration checks are often made using a second sterile microscope in the operating room. This second sterile microscope has three sets of micrometer type adjustments in order to measure the knife blade's length. The first two being adjustment in the microscope's stage in the x and y plane. Then there is a micrometer scale in the reticle of the eye piece. The time consuming nature of the set-up to measure and calibrate, often requires a nurse and a technician to set and check the length of the knife's blade. Then, the surgeon will also check the length right before making the incision.

The number of measurements and the micrometers used to measure all of a certain tolerance and variability. A stacking of tolerances due to device or person can result in incision that can be off as much as 0.100 mm or more. This calibration problem is and has been a problem in all types of Keratorefractive surgery. While the goal in Keratorefractive surgery is measure and cut for each incision and for each location on the cornea, the problems with calibration and the time delays has resulted in minimal measurement and a single depth of current being made for all incisions because setting the length of the knife once is so time consuming. Further, even when the micrometer knife is set to a desired depth, there have been problems with that measurement being off and the resulting incision being off because of the tolerance stacking noted above.

The incisions are made in quadrants of the cornea. The difficulty of calibration has resulted in a minimal number of measurements being made, in many cases only a single pachymeter measure being made at the cornea's center. The micrometer knife blade's length is attempted to be set at that particular pachymeter reading, then checked with the second microscope and by the surgeon, nurse and/or technician. Because the cornea's thickness increases from center to edge, the center reading used as a approximate or gross eighty-five percent of thickness of the cornea. With the tolerance stacking, the corneas change in thickness due to time and quadrant, many times the incisions are inadequate resulting in under correction or too deep resulting in perforation, sutures and the end of the operation. The knife blade calibration problems related to RK in particular, and Keratorefractive surgery in general, has resulted in many patients having to under go a second operation because the initial surgery was resulted in under-corrected vision or sutures due to cornea perforation.

Some surgeons do not use a second microscope to check knife blade length, but use a physical block or coin gauge. This devices measure by using physical contact of the blade as a limitation. Unfortunately, these type of gauges because of their design and intended use, can damage the knife blade.

While measure and cut is the goal, the reality of time consuming calibration of the knife blade and the cornea's thickness changing during the operation due to dehydration, precludes numerous and multiple measurements during an operation under the currently available systems.

Further and in particular to RK, several RK procedures are popular in the United States. One is known as the American method, where the initial wound is formed by plunging initially in to the edge of the optical zone, so the possibility of impinging on the optical zone incision is minimized, and the incision is made in a direction radially away from the optical zone. Another method is known as the Russian method, where the initial wound is made at the edge of the cornea and the direction of the incision is toward the optical zone. The Russian method results in less pressure during cutting and cleaner incisions, but has the danger of cutting into the optical zone. Both methods also use a different blade style, i.e. angle of blade, number of edges of the blade -the overall knife blade configuration would be a particular style. No matter the style, however, in both of these procedures, as well as others, the depth of incision has been a problem because of the current calibration problems noted above. It has not been unusual for the depth of cuts to be off anywhere from 0.050 mm to 0.100 mm or more. These calibration problems have been encountered in all types of Keratorefractive surgery, including AK, RK, HK and all incisional Keratotomy.

For example in AK surgery the cuts are usually arcuate or have T-cut designs and depth is very critical. In HK surgery, there have been hexagonal and octagonal incision designs in the cornea that should be to a specific and accurate depth. The problems with depth and under cutting and perforation .have been encountered in all types of Keratorefractive surgery. As the techniques develop and the types of incisions change, as they will in order to affect the necessary change to a particular cornea's shape, the necessary precision will have to be present in the knives even more.

Many of the current knives used diamond knife blades, where the diamond knife blade is usually 6 to 7 mm in length. This size necessary to accomplish this particular diamond size for the micrometer knife usually is manufactured from a two karat diamond. The very same size diamond that is the most popular in the world for its use in engagement rings and the like. The current invention will address the problem and cost of using such popular diamonds.

The problem is calibration and despite efforts to check the cutting blades length through the use of a optical reticle in the operating room, the X-Y plane digital micrometer adjustments needed in that type of measurement often does not reduced errors, but actually has compounded the tolerance or cut-depth problem and increased the degree and extent of under correction and perforation. Improving the accuracy of the depth of incision is critical to improving the not only the efficiency of both the American and Russian method, but all cutting methods used in Keratorefractive surgery. The present invention is directed to solving these problems and other problems, while improving the result of Keratorefractive surgery.

SUMMARY OF THE INVENTION

The invention is directed toward a novel system of surgical instruments for use in forming the requisite incisions for Keratorefractive surgery. The surgical system of the invention contains a set or series of sharp fixed length knife blades. The system contains a plurality of knife blades and handles. Instead of a single cutting blade being adjusted for incisions on different parts of the cornea and for different corneas, i.e. one tool to do everything badly. The current invention is a system having variable fixed length knife blades that are of a precise fixed length. Each fixed length knife blade being mounted on a handle, where the fixed length blade is fixed on the handle and in combination with the footplate, i.e. the footplate assembly, fixed on the handle of each instrument. The blade having a fixed length attachably connected to the footplate assembly. The knife blades of the current invention would be in a range having a minimum and a maximum length blade with various other length blades at fixed differential increments in between. A surgeon for example could have a set of knives in a range of 0.001 mm to 1 mm at 0.001 mm increments or a set of knives from 0.400 to 0.600 mm The increments will be as small and a large as necessary to accomplish the precision needed for the Keratorefractive surgical procedure in question. For example, the range of instruments in a set could have the lengths of cutting blades in a particular set could be 0.200 mm to 0.300 mm at 0.01 mm increments. Another series of instruments could be set of instruments having a range of from 0.400 to 0.500 at 0.20 mm increments. Each set would have a range and each range of knives would vary in length by a predetermined increment. Therefore, the range and increments available to the surgeon would be sufficient to satisfy the various thicknesses and depth of incisions for any particular cornea.

This system's preferred cutting blade will be made from diamond. Due to the hardness and the surface of diamond, the incisions are smoother and cleaner than other materials. New or other materials with the same or similar physical characteristics to diamond in cutting could also be used in this system. However, the current preferred embodiment uses diamond cutting blades.

The system used by a surgeon can be a set having as many fixed length knife blades as necessary for a particular surgeon's needs. One surgeon may have a system of two knives and another surgeon may have a system of two thousand knives. The system envisions the use of multiple fixed length knife blades. Again, the needs of a particular surgeon will dictate the ranges, increments and number of sets.

Another embodiment of the invention can incorporate at the footplate assembly be a particular color that would signify a style of blade. A style being for example the angle of the cutting edge, the number of cutting edges, the resulting configuration of the incision or whatever qualities that a particular style of knife blade may have, the current invention can incorporate any style of knife. Alternative embodiments to signify style would be any variation in the footplate assemblies surface or design that would make visually discernable from another footplate assembly having a blade of a different style.

Another embodiment of this invention would have the handles for a particular range be a specific color and that color varying in the range in shading or intensity as the increment of the fixed length of the knife blade changes. For example and not as any limitation of this embodiment, the range of fixed length knives in the 0.400 mm to 0.500 mm could be blue and with each change increment from the minimum length to the maximum length would be a different shade of blue or intensity of blue. The shade can go from lighter to darker or darker to lighter, or greater or lessen the intensity of the color as the increments change. This embodiment would have a particular color to a range and a particular shading or intensity of that color to a particular length blade.

Another embodiment would have the identity of the predetermined fixed length knife blade's length being etched by means of a laser or chemically. Also marking can be accomplished through stamping.

Another embodiment of this invention could incorporate just the color of the range and not incorporate the shading or intensity. Another variation could be a machining of the handles or a knurling pattern to distinguish range and/or increment. These variations of this embodiment encompass any discernable change in the visual appearance of the handle indicate of a different range and/or increment of a particular length fixed length knife blade.

Another embodiment of the system incorporates in the footplate assembly having a scale. The scale would be similar to a optical recticle scale to have the surgeon double check the length of the cutting blade selected under the operating room microscope. The scale could be partially clear, completely clear or opaque. This would further ensure the selection of the right length cutting blade, but also to ensure that the cutting blade is not misaligned. Further the scale could be the footplate itself or a scale in addition to the footplate and incorporated in to the footplate assembly.

Another embodiment of the instant invention would incorporate a system for protecting the knife blade by having the knife blade retract into the footplate assembly or have the footplate assembly retract into the handle. These embodiments would facilitate the protection of the fixed length knife blade. Further, these embodiments would facilitate the locking of the retractable knife or footplate assembly in to a closed or open position.

Another embodiment, the handle could be disposable and the footplate assembly could be quickly releasable from a disposable handle or non-disposable handle. Handles of a particular angle or shape or contour could be incorporated with a attachable footplate assembly to satisfy the differences in one surgeon's hands to another surgeon's hands.

All of the embodiments of the above could also, incorporate a portable pachymeter that would be light weight and incorporated in all and any embodiment of the invention.

The resulting Keratorefractive system would utilize any and all similar embodiments. The surgeon would select a set out of a range or series of sets of knives and use the fixed blade system to ensure exact and precise incisions. The knives would be pre-calibrated. The surgeon could make multiple cuts of varying depths along a single incision or multiple incisions of varying depths incorporating multiple measurements in a timely fashion because the calibration problems associated with current used systems would not be encountered in the instant invention and its embodiments. The instant invention provides for precise, quick and accurate method for performing Keratorefractive surgery. The present invention and its various embodiments can be utilized in all current RK surgical techniques, including the American and Russian methods.

BRIEF DESCRIPTION OF THE DRAWINGS

A better understanding of the invention can be obtained when the detailed description of the explemplary embodiment set forth below is reviewed in conjunction with the accompanying drawings in which:

FIG. 6 is a partial side view of the embodiment of an instrument of the current invention;

FIG. 7 is a partial front end view of the embodiment of FIG. 6;

FIG. 8 is a partial top view of the embodiment of FIG. 6;

FIG. 9 is a partial front view of the embodiment of FIG. 6;

FIG. 10 is a side view of an another embodiment of an instrument of the current invention;

FIG. 11 is another side view of the embodiment of FIG. 10;

FIG. 12 is another side view of the embodiment of FIG. 10;

DETAILED DESCRIPTION OF EXEMPLARY EMBODIMENTS

Figure 1:
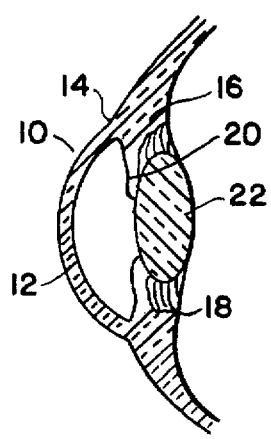
FIG. 1 is a schematic in cross-section of the human eye, in particular, the cornea and other elements defining the anterior chamber.

FIG. 1 illustrates in brief the anatomy of the human eye. The eye is designated by reference number 10. The outer surface of the eye formed by the cornea 12 which terminates at the corneal margin or limbus 14 in the vicinity of adjacent the sclera spur 16. The ciliary muscle 18 joins an iris 20 and is connected to the crystalline lens 22. The lens 22 is flexed by the ciliary muscle 18 in order to focus a subject.

Figure 2:
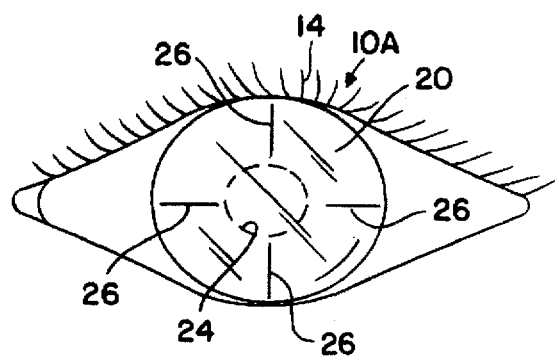
FIG. 2 is a front, schematic view of a human eye illustrating for example, certain types of typical incisions made during a Radial Keratotomy (RK) procedure.

FIG. 2 is a front view of eye 10, wherein iris 20 generally defines an optical zone, illustrated by dotted lines 24 within which light passes through the lens 22 onto the retina (not shown) for transmission of an image to the optic nerve and the brain.

Figure 3:
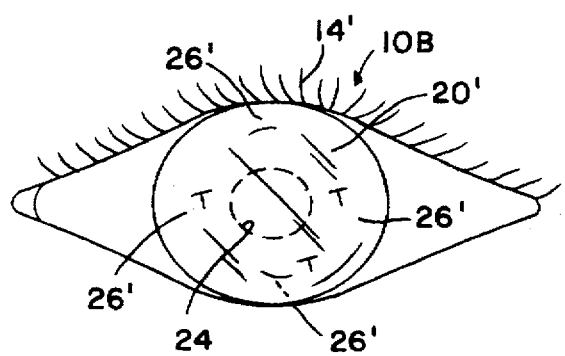
FIG. 3 is a front, schematic view of a human eye illustrating for example, certain types of typical incisions made during a Astigmatic Keratotomy (AK) procedure.
Figure 4:
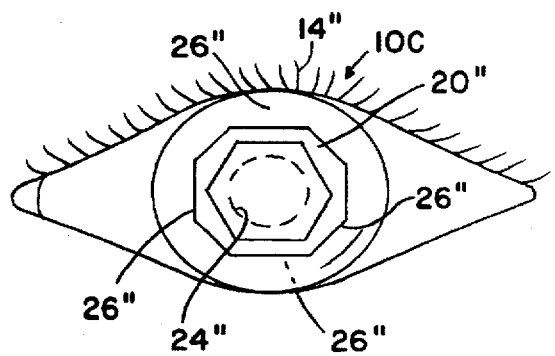
FIG. 4 is a front, schematic view of a human eye illustrating for example, certain types of typical incisions made during a Hyperopic Keratotomy (HK) procedure.

A person that is myopic or nearsighted, the cornea tends to have a curvature greater than is necessary. This excessive curvature of the cornea causes the focal point of images entering the eye to be offset from the retina. It has been found that myopia can be surgically corrected by making a number of incisions in the cornea, similar to those designated reference number 26 of FIG. 2 in a region outside the optical zone. FIGS. 3 and 4 illustrates certain typical types of incisions made during AK and HK. As the techniques for Keratorefractive surgery develop and evolve, the direction, size and configuration of any and all incisions will change or modify for a particular type of procedure. For example in FIG. 3, "T-type" and "Arcuate-type" are illustrative as too the typical types of incisions which may be used for AK. Both or one or some variation may be utilized. These types of incisions are shown by way of example and not by way of limitation as to the type, design, and/or configuration of the incisions utilized in Keratorefractive surgery or the those made by the instant invention herein.

For purposes of example and not of limitation, the embodiment discussed will be referenced in regards to RK for ease and simplicity. The present invention is applicable to any type of Keratorefractive or incisional keratotomy. RK is practiced through varying methods for making incisions 26 of FIG. 3. These methods include the American method where the knife is plunged initially at the edge of the optical zone (which is marked by the surgeon with dotted lines similar to those referenced by 24 in FIG. 2) and moved toward the limbus 14, and the Russian method where the incision is formed by moving the knife from the limbus toward the optical zone. The present invention is not limited to any specified method, but these methods being the most popular at the instant moment, are used for example.

The incisions of either method require precise control in the depth of incision. The present invention is an improvement over on the current typical keratorefractive knife used in RK procedures, and shown generally in FIG. 5, where a blade 28 is formed of a sharp hard material, in this example diamond and is mounted in a footplate assembly 30. The footplate assembly has footplates 29 that straddle the blade 28 and are designed to slide along the outer surface of the cornea 12 during procedures for all types of Keratorefractive surgery. For controlling the depth of cut the depth of cut the length of the blade 28 projects beyond the footplates 29 being controlled by a micrometer setting of a known design and shown at 27. The calibration and measurement problems and the resulting incision error has been detailed above with use of this current system.

Figure 5:
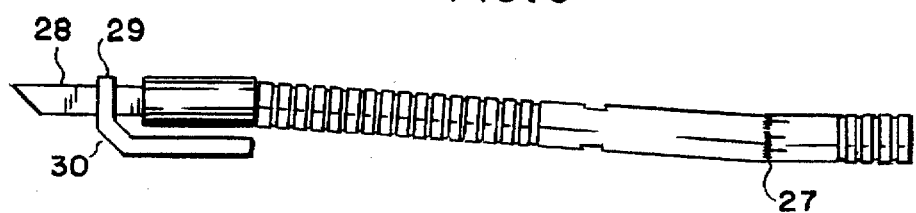
FIG. 5 is a perspective side-view of a typical current keratorefractive knife.

The present invention prevents the incision errors associated with the typical knife system of FIG. 5. FIG. 6 is a partial side view of a knife 40, that is exemplary of the current of the current invention. FIG. 6 illustrates a side view of the footplate assembly 50 having blade 52, being attachably connected by mounting piece 54 and pair of footplates 56 straddle the blade 52. The length of the blade 52 that protrudes from beyond the footplates to the tip is a predetermined length 58. The predetermined length 58 is established for each knife in the system of knives that is incorporated in the current invention. The predetermined length would be set in manufacturing the footplate assembly and attached to a handle 42. The footplate assembly can be permanently attached to a handle 42 or detachable from handle 42 for the purposes of being disposable. Further, handle 42 can be customized for a particular surgeon hand or configured a specific design, angel or whatever configuration is desired. The handle can also incorporate a quick disconnect type connection between the handle 42 and the footplate assembly 50, so that a surgeon can change handles or footplate assemblies in a quick an easy manner.

The predetermined length 58 will change from knife to knife in the system of knives of the current invention. The system can be as few as two knives to almost an infinite number of knives, depending on the incremental change between the predetermined length from knife to knife. The system can be utilized in system of knives having a particular range and that particular range having a fixed increment from knife to knife. For example, the system of the present invention could be a set of knives in a range having a minimum predetermined length of 0.300 mm to a maximum predetermined length of 0.500 mm at 0.010 mm increment length variation from knife to knife. As a result, these series of knives would be in a system of 21 knives having 21 different predetermined fixed length blades. The predetermined length in this illustration would vary from 58a to 58u. Furthermore, the total available knives in a set could vary in number anywhere from two to however many knives are required by a particular surgeon.

An embodiment could include a series of knives 40 have a knife blade of a predetermined length starting at a minimum of 0.001 mm to a maximum predetermined length of 2 mm at 0.001 mm increments or a series of 200 knives within the system of the current invention. Obviously, the variation of the number of knives in a system can vary further by the different styles of blades.

For the purpose of example, the footplate assembly 50 could be varied by angle of the knife blade 52's edge, the number of knife blade edges that knife blade 52 may have, the thickness of knife blade and the configurations of knife blade 52 can be varied to meet any particular need. The current invention is suitable for any configuration for knife blade 52 because the present invention to directed towards that knife blade having a fixed predetermined length, so that the incision made in the cornea is at the depth of the predetermined length 58. Further the footplate assembly 50 can be constructed to have a single footplate straddling blade 52. The system of the current invention is flexible to meet the knife configuration requirements for any particular Keratorefractive procedure.

An alternative embodiment of the current invention is illustrated by FIGS. 10, 11, and 12. FIG. 10 illustrates a knife 60 of the current invention wherein the footplate assembly 70 can retract into handle 65 and be locked in a closed position as illustrated by FIG. 10. FIG. 10 shows the knife 60 where the footplate assembly 70 is retracted in the handle 65 and the footplate assembly is locked in place inside the handle by the locking configuration 80. The locking configuration incorporates a pin 82 and a channel 84 wherein the retractable cover piece 66 can be slidably moved in to the closed position of FIG. 10.

The footplate assembly 70 can be extended and exposed for use by turning piece 66 and slidably retracting piece 66 along channel 84 into an open position as illustrated by FIG. 11. The pin 82 would lock in place at the other end of channel 82 to fixablly hold piece 66 in the open position for use during Keratorefractive surgery.

In another embodiment of the invention, the range of the knives within a series of the system can be identified by a discernable visual differences on the surface of the knives handles. This embodiment can be illustrated at FIG. 13, wherein FIG. 12 shows knife 100 having a surface finish 120. Surface finish 120 could be a particular color for a specific range. The increment change in the range can be signified by varying the shading or intensity of the particular color for a range. For example, the range for the series of knives in the range 0.400 mm to 0.500 mm may be blue and the handle at 120 could go from a lighter blue to a darker blue as the predetermined fixed length blade 115 of footplate assembly 110, goes from a minimum of 0.400 mm to 0.500 mm at whatever increment that is desired. The color at 120 would signify the particular range of a blade and the size of the predetermined length 115. Further, the knife 100 could have laser or mechanically stamped or similar means of identification the actual length of the predetermined fixed length blade at 125 and at end 126. 125 and/or 126 would be marked with the identifying length, i.e., 0.450 mm. The visual identification of predetermined length of blade from knife to knife could be by color or etching or knurling or any manner where one knife can be visually discernable from another knife to signify the particular predetermined length.

Another embodiment could have the foot plate assembly identify the style of the predetermined fixed length blades incorporated in those assemblies. The identification would be any visually discernable way to distinguish one foot plate assembly from another in order to identify a different style of knife as to angle of blade, design of footplate assembly, or any configuration as to the relationship of the incision and the instrument. The visual discernable difference could be accomplished through the use of color or etched pattern or knurling or any physically discernable identification that would illustrate a difference and signify one style from another.

Figure 13:
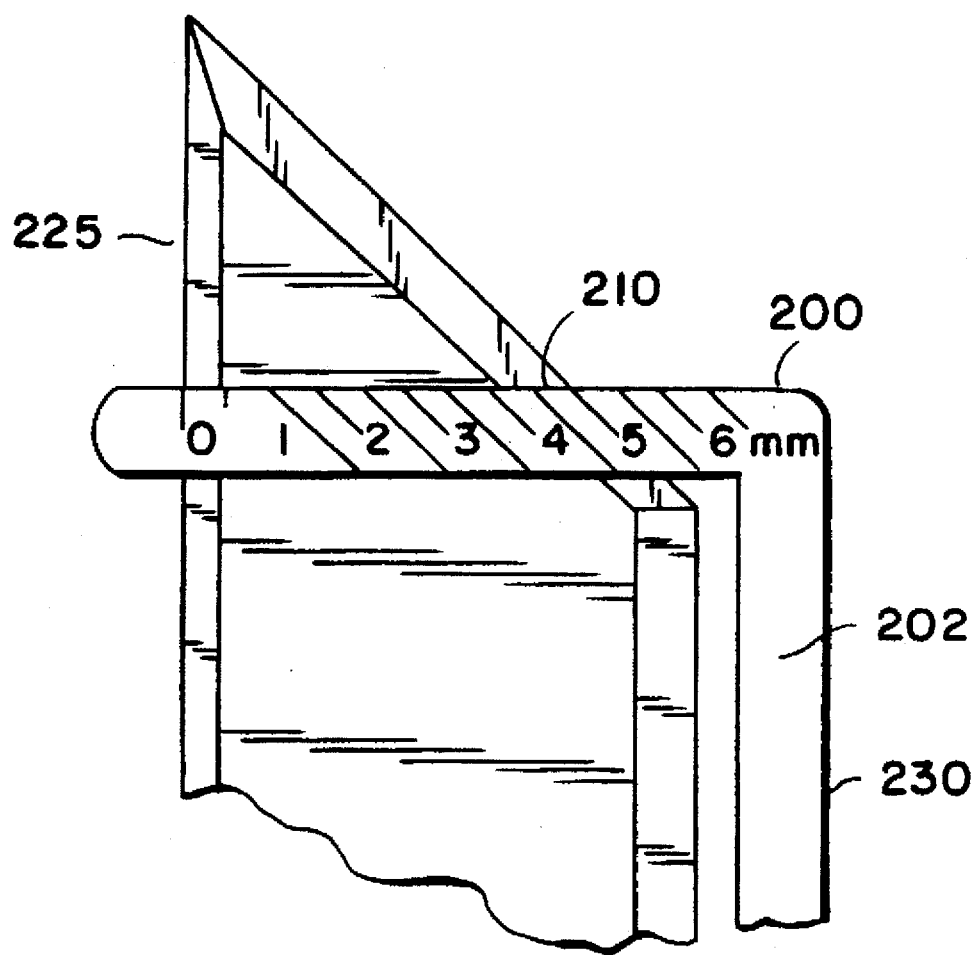
FIG. 13 is a partial side view of another embodiment of the current invention.

FIG. 13 illustrates a scale 200 incorporated on the perpendicular axis of the footplate 210 relative to the predetermined fixed length knife blade 225 of a footplate assembly 230. The scale can also be incorporated on the parallel axis at 202 of the footplate 210. Further, the footplate could be partially or completely clear so that the predetermined fixed length knife blades could be read right through the clear scale with the use of the reflection of light off the predetermined fixed length knife blade.

All of the knife blades are preferably to be manufactured from diamonds at this time, but the invention is suitable for use with predetermined fixed length knife blades manufactured from any and all surgical knife materials, including stainless steel; high alloy steel; other precious stones such as, but not limited to ruby, sapphire, and emerald; and any material which will result in an incision of the type that will affect the eye's cornea in order to improve .vision defects in the eye. It has been determined that diamonds and similar materials are currently utilized because there use result in clean and precise incisions. It could develop that Keratorefractive surgery will require less precise wounds, but still at a precise depth and the current invention would be suitable for those instances.

A benefit, however, of the current invention is that each knife will use significantly smaller diamond than the knife 40 of FIG. 3. The knives of the type of FIG. 3 are often manufacture from 2 karat diamonds, the most popular diamonds in the world because they are used for engagement rings and the like. The current invention can utilize diamond chips, re-processed diamonds or re-cut diamonds because of the use of the predetermined fixed length knife blade. As a result, the current invention broadens the available supply of usable diamonds for knife blades.

It should be understood that there can be improvements and modifications made to the embodiments of the invention described in detail above without departure from the spirit or scope of the invention, as set forth in the accompanying claims.

I claim:

1. A set of surgical instruments for performing Keratorefractive eye surgery, said Keratorefractive eye surgery for changing refraction of a cornea by making a plurality of incisions in said cornea, and said set of surgical instruments for providing precise depth of each of said plurality of incisions, said set of surgical instruments comprising:

at least two knife blades for making said plurality of incisions, each of said two or more knife blades having a cutting portion of a precise fixed length, said precise fixed length of each of said at least two knife blades differing by a predetermined increment from said precise fixed length any other of said two or more knife blades; and two or more footplate assemblies, each of said two or more footplate assemblies for attachably holding one of said two or more knife blades such that said cutting portion of said one of said two or more knife blades extends from said footplate assembly by said precise fixed length, said precise fixed length for providing said precise depth of each of said plurality of incisions.

2. The set of surgical instruments of claim 1 wherein each of said at least two footplate assemblies further comprises a handle for holding and manipulating said two or more footplate assemblies.

3. The set of surgical instruments of claim 1 wherein each of said at least two footplate assemblies further comprises a first marker for indicating a range having a minimum value, and wherein said precise fixed length of each of said two or more knife blades is less than said maximum value and greater than said minimum value of said range.

4. The set of surgical instruments of claim 3 wherein said first marker further comprises a first visual identification system for visually identifying said range.

5. The set of surgical instruments of claim 4 wherein said first visual identification system farther comprises a color for visually identifying said range.

6. The set of surgical instruments of claim 3 wherein said first marker further comprises a first visual identification system for visually identifying said range and said precise fixed length of each of said at least two knife blades.

7. The set of surgical instruments of claim 6 wherein said first visual identification system further comprises a color having a plurality of shades, said color for visually identifying said range and each of said plurality of shades is for visually identifying said precise fixed length of each of said at least two knife blades.

8. The set of surgical instruments of claim 3 wherein said first marker further comprises a first visual identification system for visually identifying said precise fixed length of each of said at least two knife blades.

9. The set of surgical instruments of claim 8 wherein said visual identification system further comprises a color having a plurality of shades for visually identifying said precise fixed length of each of said at least two knife blades.

10. The set of surgical instruments of claim 8 wherein said first visual identification system further comprises a scale for visually identifying said precise fixed length of each of said at least two knife blades.

11. The set of surgical instruments of claim 1 wherein said at least two footplate assemblies further comprises a second marker for indicating a style of said cutting portion of said cutting portion of said at least two knife blades.

12. The set of surgical instruments of claim 11 wherein said second marker further comprises a second visual identification system for visually identifying said style of said cutting portion of said at least two knife blades.

13. The set of surgical instruments of claim 12 wherein said style of said cutting portion of said at least two knife blades further comprises a cutting angle.

14. The set of surgical instruments of claim 12 wherein said style of said cutting portion of said at least two knife blades further comprises a number of cutting edges.

15. The set of surgical instruments of claim 12 wherein said style of said cutting portion of said at least two knife blades further comprises a configuration of said plurality of incisions.

16. The set of surgical instruments of claim 1 wherein said at least two footplate assemblies each further comprise a footplate which straddles said cutting portion of one of said at least two knife blades, said footplate for sliding over said cornea in order to control said precise depth of each of said plurality of incisions.

17. A set of surgical instruments for performing Keratorefractive eye surgery, said Keratorefractive eye surgery for changing refraction of a cornea by making a plurality of incisions in said cornea, and said set of surgical instruments for providing precise depth of each of said plurality of incisions, each of said set of surgical instruments comprising:

a knife blade for making said plurality of incisions, said knife blade having a cutting portion of a precise fixed length, said precise fixed length of said cutting portion of said knife blade differing by a predetermined increment from said precise fixed length of said cutting portion of any other knife blade of said set of surgical instruments;

a footplate assembly for attachably holding said knife blade such that said cutting portion of said knife blade extends from said footplate assembly by said precise fixed length of said cutting portion, said precise fixed length of said cutting portion having a value greater than eighty-five percent of a measured thickness of a region of said cornea and less than said measured thickness of said region of said cornea, said precise fixed length for providing said precise depth of each of said plurality of incisions, said footplate assembly including a first visual identification system for visually identifying said precise fixed length of said cutting portion of said knife blade, and said footplate assembly including a second visual identification system for visually identifying a style of said cutting portion of said knife blade; and a handle for holding and manipulating said footplate assembly.

18. The set of surgical instruments of claim 17 wherein said first visual identifications system further comprises a color having a plurality of shades for visually identifying said precise fixed length of said knife blade.

19. The set of surgical instruments of claim 17 wherein said first visual identification system further comprises a scale for visually identifying said precise fixed length of said knife blade.

20. The set of surgical instruments of claim 17 wherein said style of said cutting portion of said knife blade further comprises a cutting angle.

21. The set of surgical instruments of claim 17 wherein said style of said cutting portion of said knife blade further comprises a number of cutting edges.

22. The set of surgical instruments of claim 17 wherein said style of said cutting portion of said knife blade further comprises a configuration of said plurality of incisions.

23. The set of surgical instruments of claim 17 wherein said footplate assembly further comprises a footplate which straddles said cutting portion of said knife blade, said footplate for sliding over said cornea in order to control said precise depth of each of said plurality of incisions.

24. A method for performing Keratorefractive eye surgery, said Keratorefractive eye surgery for changing refraction of a cornea by making a plurality of incisions in said cornea, and said method for providing a precise depth of each of said plurality of incisions, said method comprising the steps of:

marking an optical zone of said cornea;

measuring a precise thickness of a region of said cornea, said region not including said optical zone of said cornea;

selecting a surgical instrument from a set of surgical instruments, said selected surgical instrument including a footplate assembly for attachably holding a knife blade such that a cutting portion of said knife blade extends from said footplate assembly by a precise fixed length, said precise fixed length of said knife blade having a value greater than eighty-five percent of said precise thickness of said region of said cornea and less than said precise thickness of said region of said cornea, and said precise fixed length for providing said precise depth of each of said plurality of incisions;

making at least one incisions in said region of said cornea using said selected surgical instrument; and repeating said steps of said method for performing Keratorefractive eye surgery, thereby changing said refraction of said cornea.

25. The method of claim 24 wherein said step of making at least one incisions in said region of said cornea using said selected surgical instrument further comprises the step of making at least one incisions in said region between said optical zone and a limbus of said cornea.

26. The method of claim 25 wherein said step of making at least one incisions in said region between said optical zone and a limbus of said cornea further comprises the step of making said at least one incisions in a first direction from said optical zone toward said limbus of said cornea.

27. The method of claim 25 wherein said step of making at least one incisions in said region between said optical zone and a limbus of said cornea further comprises the step of making said at least one incisions in a first direction from said limbus toward said optical zone of said cornea.

* * * * *